United States Patent [19]

Schoeffel

[11] Patent Number: 5,503,554

[45] Date of Patent: Apr. 2, 1996

[54] ENDODONTIC FILES

[76] Inventor: G. John Schoeffel, P.O. Box 370, Dana Point, Calif. 92629

[21] Appl. No.: 419,813

[22] Filed: Apr. 11, 1995

[51] Int. Cl.$^6$ ........................................ A61C 5/02
[52] U.S. Cl. ................................................. 433/102
[58] Field of Search ............................ 433/102, 224

[56] References Cited

U.S. PATENT DOCUMENTS

| | | | |
|---|---|---|---|
| 4,518,356 | 5/1985 | Green | 433/102 |
| 4,971,556 | 11/1990 | Ritano | 433/102 |
| 5,017,138 | 5/1991 | Schilder | 433/102 |
| 5,026,284 | 6/1991 | Martin | 433/102 |
| 5,219,284 | 6/1993 | Velvart et al. | 433/102 |
| 5,257,934 | 11/1993 | Cossellu | 433/102 |

FOREIGN PATENT DOCUMENTS 0257961  3/1988  European Pat. Off. ............ 433/102

*Primary Examiner*—Nicholas D. Lucchesi
*Attorney, Agent, or Firm*—Blakely, Sokoloff, Taylor & Zafman

[57] ABSTRACT

Endodontic files which provide constant dentin volume removal from file to file based on the actual volume of dentin removed from file to file. Each file removes exactly the same increase in volume as its predecessor. In this manner, a clinician may use each file in a sequential manner from smallest to largest without the need to alternate sizes or rely on subjective factors. Correspondingly, the time required to prepare a patient's root canal drops as a function of the reduced need to interchange sizes along the way and provide a clinical method of preparing root canals that relies on objective clinical techniques.

4 Claims, 1 Drawing Sheet

ENDODONTIC FILES

BACKGROUND OF THE INVENTION

1. Field of the Invention

The invention is in the field of endondtic files.

2. Description of the Prior Art

Endodontic Files—Overview

In the middle of every tooth is a small tube, referred to as the root canal, approximately one inch long and varying in diameter from the diameter of a piece of angel hair spaghetti to the diameter of a human hair. This tube in normally filled with healthy tissue, but for a variety of reasons this tissue can become inflamed, infected and die. In order to remove the dead or dying tissue, the root canal must be "drilled out" or enlarged with special dental instruments until a clean tube is established that can be filled with a permanent hermetic material. The instruments used to accomplish this objective are called "endodontic files".

Prior to 1959, endodontic files were not manufactured according to any set standards. That is, the size, shape and overall configuration varied from manufacturer to manufacturer.

During 1959, a standard known as variable linear dimensional (VLD) standardization came into being. Endodontic files manufactured after 1959 were defined by the diameter of the file at a point approximately 1 mm from the tip (D1) as shown in FIG. 1. An endodontic file with a diameter of 0.10 m at D1 is designated as a number 10 instrument; an endodontic file with a diameter of 0.15 at D1 is designated as a number 15 instrument, etc. Endodontic files between a #6 and a #10 increase in size 0.02 mm per file size, from the #10 endodontic file to the #60 endodontic file, each one in the series increases by 0.05 mm, and after endodontic file #60 each one increases by 0.10 mm at D1. This sizing system has become the ISO (International Standards Organization) standard. The taper is also defined by the standard and is determined as follows. A point 15 mm from D1 is designated D2 as shown in FIG. 1. At D2, the diameter of each file is 0.30 mm greater than the diameter of the file at D1. There is a linear increase in diameter from D1 to D2 so that for each 1 mm increase in length, there is a 0.02 mm increase in diameter. It should be noted that the 15 mm height or D1–D2 distance and the 0.30 mm relationship between D1 and D2 is simply a standard or tradition and of little clinical significance. In other words, the D1–D2 distance and D1–D2 relationship could be other than 15 mm and 0.30 mm respectively and beneficial results could still be obtained.

During 1991 a new endodontic file sizing system known as constant percent (CP) came into being. The constant percent change sizing system was the first change in endodontic file size standardization in over thirty years and is based on changing the diameter of D1 by an exact percentage. The CP system came into being because for a myriad of clinical reasons, the diameter of many root canals has decreased since 1962. Accordingly, endodontic treatment became more and more difficult since the introduction of the variable linear dimensional standardization. Specifically, since endodontic instruments were used by hand or, as explained below, in oscillating tools, it was becoming increasingly difficult to treat the more difficult endodontic cases. The problem with the VLD system is that the percentage change from file size to file size is erratic under the VLD sizing system. For example, the percentage change of D1 from a #8 endodontic file to a #10 endodontic file is 20%, from a #10 endodontic file to a #15 endodontic file the change is 50%, and from a #15 endodontic file to a #20 endodontic file the change is 33%. In order to rectify this shortcoming, the CP change system was introduced and is based on a constant percent change from one file size to the next. Each D1 is exactly x% larger than the its predecessor, where x is chosen so that a root canal treatment is accomplished while minimizing the number of instruments needed to perform the root canal treatment. In this connection, in the currently utilized CP system, x is 29.17%. Additionally, files currently produced under the CP system utilize a D1 to D2 differential of 0.6 mm instead of 0.3 mm as is the case with files produced under the VLD system. The CP system seemingly provides a smoother transition from one file to the next since each file is the same percentage larger than its predecessor. A paper describing the CP system is entitled "Revolutionary New Concepts In Endodontic Instruments Sizing" by Herbert Schilder in *Giornale Italiano di Endodonzia*, Vol 7, No 4, 1993.

Tables 1 and 2 below shows the D1 and D2 diameters for a typical VLD and CP file system respectively, along with a percentage change of D1 diameters and the volume and percentage volume change between adjacent files between adjacent files in each system.

TABLE 1

| D1 Increment | VLD D1 diameter | Diameter % Change | VLD D2 diameter | VLD Volume | Volume % Change |
| --- | --- | --- | --- | --- | --- |
|  | 0.150 |  | 0.450 | 1.15 |  |
| 0.0500 | 0.200 | 33% | 0.500 | 1.53 | 33% |
| 0.0500 | 0.250 | 25% | 0.550 | 1.97 | 29% |
| 0.0500 | 0.300 | 20% | 0.600 | 2.47 | 25% |
| 0.0500 | 0.350 | 17% | 0.650 | 3.03 | 23% |
| 0.0500 | 0.400 | 14% | 0.700 | 3.65 | 20% |
| 0.0500 | 0.450 | 13% | 0.750 | 4.33 | 19% |
| 0.0500 | 0.500 | 11% | 0.800 | 5.07 | 17% |
| 0.0500 | 0.550 | 10% | 0.850 | 5.86 | 16% |
| 0.0500 | 0.600 | 9% | 0.900 | 6.72 | 15% |
| 0.1000 | 0.700 | 17% | 1.000 | 8.60 | 28% |
| 0.1000 | 0.800 | 14% | 1.100 | 10.72 | 25% |
| 0.1000 | 0.900 | 13% | 1.200 | 13.08 | 22% |
| 0.1000 | 1.000 | 11% | 1.300 | 15.67 | 20% |

TABLE 2

| D1 Increment | Constant Pct D1 diameter | Diameter % Change | Constant Pct D2 diameter | Constant Pct Volume | Volume % Change |
| --- | --- | --- | --- | --- | --- |
|  | 0.129 |  | 0.729 | 2.52 |  |
| 0.0380 | 0.167 | 29% | 0.767 | 2.92 | 16% |
| 0.0490 | 0.216 | 29% | 0.816 | 3.49 | 19% |
| 0.0630 | 0.279 | 29% | 0.879 | 4.30 | 23% |
| 0.0810 | 0.360 | 29% | 0.960 | 5.49 | 27% |
| 0.1050 | 0.465 | 29% | 1.065 | 7.25 | 32% |
| 0.1350 | 0.600 | 29% | 1.200 | 9.90 | 37% |
| 0.1750 | 0.775 | 29% | 1.375 | 13.97 | 41% |
| 0.2250 | 1.000 | 29% | 1.600 | 20.26 | 45% |

Also of note is that in 1993 endodontic files made of an alloy of nickel and titanium transformed the traditional methods of endodontic instrumentation and preparation. Endodontic files (referred to as reamers when used in a rotary mode in which case the flutes are duller than is the case with files which operate in a reciprocating mode) made from this alloy were, for the first time ever, capable of being used in a rotating dental drill. However, their use in an endodontic rotary mode created a new problem. As it turns out, rotating files or reamers can only predictably remove a specific volume of dentin (root material) per file pass. Since both prior art sizing systems (VLD and CP) remove irregular volumes per file size, as shown in Tables 1 and 2, clinical "workarounds" had to be employed in order to prepare root canals when using rotary files or reamers based on this geometry. For example, accordingly to one leading manufacturer's instructions, the reamers must be used repeatedly in a complicated protocol of alternating sizes in order to achieve the goal of preparing the root canal system when using the rotary technique.

SUMMARY OF THE INVENTION

The present invention is directed to endodontic files which provide constant dentin volume removal from file to file or from reamer to reamer. Although the CP sizing system reflects a constant percent change from one Dt to the next, it does not consider the actual volume of dentin removed by each successive file. The invented constant volume removal (CVR) sizing system is based on the actual volume of dentin removed from file to file. Each file removes exactly the same increase in volume as its predecessor-there are no irregular increases in volume removal like those encountered in both prior art systems. The clinical results are dramatic because the practitioner can, for the first time, use each file in a sequential manner from smallest to largest without the need to alternate sizes or rely on subjective factors. Correspondingly, the time required to prepare a patient's root canal drops as a function of the reduced need to interchange sizes along the way.

Upon first look, the CP file sizing system used in endodontics today seems to make logical sense. However, if the actual volume of dentin (root structure) removed between files is calculated, the inconsistencies become apparent. For example the currently available CP file system increases the D1 diameter at a rate of 29.17%. At this increase in size, the difference in dentin removal between each file varies from approximately 16% between the first two sizes and approximately 45% between the last two sizes as shown in Table 2 above. However, the difference between the volume removed between CVR files is always the same. This constant change in volume removal from one size to the next results in a smoother transition from file size to file size under clinical conditions.

Use of the CVR system:

1. Reduces preparation time.
2. Reduces metal fatigue of the endodontic files.
3. Eliminates need for Crown-down preparation.
4. Provides a less subjective technique.

The reason for developing the CVR system of endodontic file design is to allow the clinician to objectively and quickly prepare a root canal space. This is achieved by proceeding in a step-by-step manner from one endodontic file size to the next. This is not the case with the other systems. For example, from a review of the instructions for a typical CP system, it is clearly apparent that the subjective judgment of the clinician is extremely important. In particular, the clinician is instructed to start with an endodontic file two sizes larger than the endodontic file most likely to work the apex (end of the root canal). This is a very empirical determination and must be based on considerable experience. Then through a series of passes of decreasing file sizes (again based on subjective assessment) the endodontic files are taken to the apex.

Additionally, the instructions for a typical CP system call for repeating this series of steps if the clinician is unable to achieve full canal length, again an extremely subjective evaluation. In contradistinction, by the time a clinician using the CP system of files has achieved working length, a clinician using the CVR system would have completed the preliminary filing through a progressive series of files designed to remove exactly the same volume of dentin with every pass. That is, for a typical CP procedure, 5–6 files are used per root canal, but they are rotated so that there are about 30 file changes per root canal. On the other hand, for a typical CVR procedure, 10–12 files are used per root canal, but each file is used only once per root canal.

The CVR system provides a clinical method of preparing root canals that relies on objective clinical techniques. For example, when using the CVR system, once the length of the root canal is determined (from a completely objective measurement), then each file is used sequentially from beginning to end at exact working distances. On the other hand the directions for using the CP system are filled with subjective guidelines.

DETAILED DESCRIPTION OF THE INVENTION

The present invention is directed to endonontic files which are manufactured so that each endondontic file in a series of files removes a volume of dentin which is substantially equal to the volume of dentin removed by the immediately prior file in the series. Endodontic files manufactured based on the present invention are manufactured in the same manner as prior art endodontic files excepting that the diameter of each file at D1, which is a point 1 mm from the tip of the file, is chosen so that with increasing D1 diameters, the volume formed by the frustum which exists between the D1 and D2 diameters increases by the same percentage between files. However, the inventive concepts apply equally to endontic files having D1 and D2 diameters defined in some other way than having a D1–D2 distance of 15 mm and a D1–D2 relationship such that D2 is 0.30 mm greater than D1. However, for simplicity, the invention is described herein utilizing the standard or traditional relationships between D1 and D2.

Figure 1:
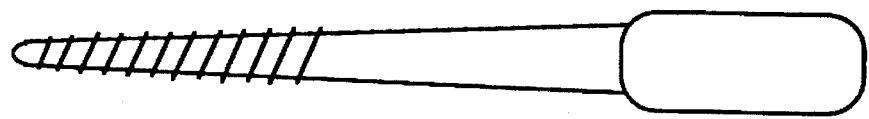
FIG. 1 is an illustration of a typical endodontic file showing the relationships between D1 and D2.
Figure 2:
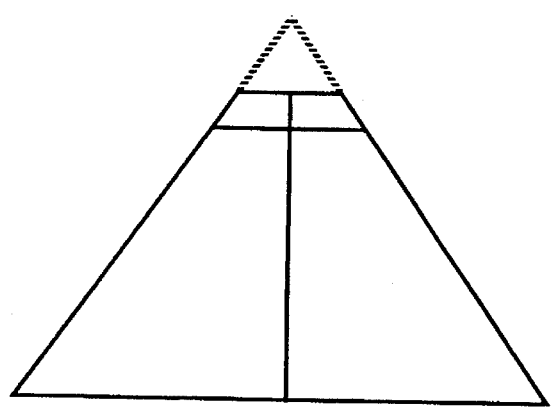
FIG. 2 is a further illustration showing the relationships between D1 and D2 and the terms used to calculate volume removal.

Although the file has ridges or threads, in use, the volume of dentin which is removed when the file is inserted through a centerline in a root canal can be calculated by determining the volume of the frustum which is formed by the file between diameters D1 and D2. The formula for the volume of a frustum is:

$$\pi \frac{h}{3} (r_1^2 + r_1 r_2 + r_2^2) \qquad \text{EQ-1}$$

where $r_1$ is the radius at D1, $r_2$ is the radius at D2 and h is the distance between D1 and D2 (with all variables in millimeters) as shown in FIG. 2. Referring now to Table 3, assuming an initial D1 of 0.15 mm, $r_1$=0.075, and, assuming D2 is 0.3 mm greater than D1, r2 is 0.15 mm greater than $r_1$ (since D2=D1+0.30 mm, $r_2$= (D1+0.30)/2=D1/2+0.15=$r_1$+ 0.15). With these assumed values, the initial volume is calculated as follows:

$$\pi \frac{15}{3} (.075^2 + .075*.225 + .225^2) = 1.14864 = 1.15 \qquad \text{EQ-2}$$

Assuming that a constant volume increase of 12% is desired, the next $r_1$ may be calculated by solving for $r_1$ in the formula:

$$\pi \frac{15}{3}(r_1^2 + r_1*(r_1 + .15) + (r_1 + .15)^2) = 1.149*1.12 = 1,287 = 1.29$$

Assuming the next $r_1$ is designated $r_x$, the resulting formula is:

$$r_x = -.15 \pm \sqrt{\frac{.0225 - \left(4\left(\frac{.0225}{3} - 1.12\left(.005625 + .01125 + \frac{.0225}{3}\right)\right)\right)}{2}} \qquad \text{EQ-3}$$

Table 3 shows the results of such a calculation which is repeated for successive $r_1$ values.

TABLE 3

| D1 Incre-ment | Constant Vol D1 Diameter | Diameter % Change | Constant Vol D2 Diameter | Constant Vol Volume | Volume % Change |
|---|---|---|---|---|---|
|  | 0.150 |  | 0.450 | 1.15 |  |
| 0.0190 | 0.169 | 12.67% | 0.469 | 1.29 | 12% |
| 0.0200 | 0.189 | 11.83% | 0.489 | 1.44 | 12% |
| 0.0210 | 0.210 | 11.11% | 0.510 | 1.62 | 12% |
| 0.0220 | 0.232 | 10.48% | 0.532 | 1.81 | 12% |
| 0.0230 | 0.255 | 9.91% | 0.555 | 2.02 | 12% |
| 0.0250 | 0.280 | 9.80% | 0.580 | 2.27 | 12% |
| 0.0260 | 0.306 | 9.29% | 0.606 | 2.54 | 12% |
| 0.0210 | 0.327 | 6.86% | 0.627 | 2.77 | 9% |
| 0.0220 | 0.349 | 6.73% | 0.649 | 3.02 | 9% |
| 0.0220 | 0.371 | 6.30% | 0.671 | 3.29 | 9% |
| 0.0240 | 0.395 | 6.47% | 0.695 | 3.59 | 9% |
| 0.0404 | 0.435 | 10.23% | 0.735 | 4.13 | 15% |
| 0.0426 | 0.478 | 9.78% | 0.778 | 4.73 | 15% |
| 0.0470 | 0.525 | 9.83% | 0.825 | 5.46 | 15% |
| 0.0490 | 0.574 | 9.33% | 0.874 | 6.26 | 15% |
| 0.0530 | 0.627 | 9.23% | 0.927 | 7.20 | 15% |
| 0.0570 | 0.684 | 9.09% | 0.984 | 8.28 | 15% |
| 0.0610 | 0.745 | 8.92% | 1.045 | 9.53 | 15% |
| 0.0780 | 0.823 | 10.47% | 1.123 | 11.24 | 18% |
| 0.0850 | 0.908 | 10.33% | 1.208 | 13.28 | 18% |
| 0.0920 | 1.000 | 10.13% | 1.300 | 15.67 | 18% |
| 0.1000 | 1.100 | 10.00% | 1.400 | 18.50 | 18% |
| 0.1080 | 1.208 | 9.82% | 1.508 | 21.81 | 18% |

It will be noted that at a D1 diameter of 0.327, the volume percentage change is 9%, at a D1 diameter of 0.435, the volume percentage change is 15% and at a D1 diameter of 0.823, the volume percentage change is 18%. In this connection, in the preferred embodiment of the invention, the volume percentage change is only constant within a range of file sizes. The reason it is preferable that the volume percentage change be constant only within a range of file sizes is that once the root canal has been partially cleared by an initial set of files, subsequent uses of the file system can usually have an increased percentage of volume removed while maintaining approximately the same amount of force on the file. However, after an initial clearing using a set of files with a constant volume removal percentage of 12%, due to characteristics of the material employed to make the files, it may be preferable to reduce the constant volume removal percentage to 9% as shown in Table 3. However, it should be understood that the specific percentages employed may vary from those shown in Table 3 depending on the material used to make the files. The only limitation regarding the specifics of the construction of the files is that the D1 diameter be chosen so that the resulting volume of the D1–D2 frustum changes at a constant percentage for a subset of files within the complete file system.

I claim:

1. A set of endodontic files, each having a tip end and a diameter D1 at a point a first predetermined distance from the tip end and a diameter D2 at a second predetermined distance from the point at the first predetermined distance from the tip end, with the diameter increasing substantially uniformly between D1 and D2 such that an initial file in the set has a volume equal to V for a frustum formed by the file between D1 and D2, and each subsequent file in the set has a corresponding volume which is the same predetermined percentage greater than the corresponding volume for its immediate predecessor file.

2. The set of endodontic files defined by claim 1 wherein the set of files comprises a plurality of subsets of files such that within each of said subsets, an initial file in the subset has a volume equal to V for a frustum formed by the file between D1 and D2, and each subsequent file in the subset has a corresponding volume which is the same predetermined percentage greater than the corresponding volume for its immediate predecessor file in that subset.

3. The set of endodontic files defined by claim 2 wherein the volume percentage change between each file within each of said subsets is constant, with said constant being different for each of said subsets.

4. The set of endodontic files defined by claim 1 wherein the first predetermined distance is approximately 1 mm, the second predetermined distance is 15 mm, and for each file in the set D2 is 0.30 mm greater than D1.

\* \* \* \* \*

UNITED STATES PATENT AND TRADEMARK OFFICE
CERTIFICATE OF CORRECTION

PATENT NO.  : 5,503,554
DATED       : April 2, 1996
INVENTOR(S) : G. John Schoeffel It is certified that errors appear in the above-identified patent and that said Letters Patent is hereby corrected as shown below:

In column 1 at line 30 please delete " m " and insert -- mm --.

In column 5 at line 7 please delete " 1,287 " and insert -- 1.287 --.

Signed and Sealed this

Twenty-third Day of July, 1996

Attest:

BRUCE LEHMAN

*Attesting Officer*           Commissioner of Patents and Trademarks